United States Patent [19]

Steen

[11] Patent Number: 5,065,746

[45] Date of Patent: Nov. 19, 1991

[54] EXPIRATION VALVE CONTROL ARRANGEMENT FOR A VENTILATING APPARATUS

[75] Inventor: Hans-Wilhelm Steen, Zarpen, Fed. Rep. of Germany

[73] Assignee: Drägerwerk, Lübeck, Fed. Rep. of Germany

[21] Appl. No.: 374,065

[22] Filed: Jun. 30, 1989

[30] Foreign Application Priority Data

Jul. 7, 1988 [DE] Fed. Rep. of Germany ....... 3822949

[51] Int. Cl.$^5$ ........................ A62B 9/02; A61M 16/00
[52] U.S. Cl. ........................... 128/205.24; 128/204.26; 128/204.18
[58] Field of Search ................... 128/205.19, 205.24, 128/204.26, 204.18

[56] References Cited

U.S. PATENT DOCUMENTS

| | | | |
|---|---|---|---|
| 3,385,295 | 5/1968 | Beasley | 128/205.24 |
| 3,486,502 | 12/1969 | Wilson | 128/205.24 |
| 3,905,362 | 9/1975 | Eyrick et al. | 128/205.19 |
| 4,190,045 | 2/1980 | Bartels | 128/205.24 |
| 4,227,523 | 10/1980 | Warnow et al. | 128/205.24 |
| 4,454,893 | 6/1984 | Orchard | 128/205.24 |
| 4,813,409 | 3/1989 | Ismach | 128/205.24 |

FOREIGN PATENT DOCUMENTS

| | | | |
|---|---|---|---|
| 2525359 | 12/1975 | Fed. Rep. of Germany . | |
| 2573658 | 5/1986 | France | 128/205.24 |

*Primary Examiner*—Edgar S. Burr
*Assistant Examiner*—Kimberly L. Asher
*Attorney, Agent, or Firm*—Walter Ottesen

[57] ABSTRACT

The invention is directed to an expiration valve control arrangement for a ventilating apparatus. The control arrangement includes a control valve for generating a control pressure in the control chamber of an expiration valve. The control valve includes a connecting passage supplied from a control gas source via a control gas line. The connecting passage opens into an outflow chamber of the control valve and the outflow chamber has an outlet to the ambient. The control valve is configured so that the dynamic end expiratory overpressure can be compensated. For this purpose, the connection passage of the control valve includes a throttle generating an underpressure and a pressure line extends from this throttle and opens into the control chamber of the expiration valve. A closure force is applied to a closure element at the outlet of the connection passage. The closure element coacts with the throttle with the underpressure being adjusted by adjusting the closure force on the closure element. The valve chamber of the expiration valve is connected to a device generating an underpressure.

11 Claims, 3 Drawing Sheets

EXPIRATION VALVE CONTROL ARRANGEMENT FOR A VENTILATING APPARATUS

FIELD OF THE INVENTION

The invention relates to a expiration valve control arrangement for generating a control pressure for operating a expiration valve. The control valve has a connection fed from a control gas source via a control gas line. The connection opens into an outflow chamber via a closure element which generates a changeable control gas flow pressure. The outflow chamber is provided with an outlet to the ambient.

BACKGROUND OF THE INVENTION

A ventilating apparatus with a control valve for driving a expiration valve is disclosed in published German Patent Application DT 25 25 359 Al.

In this known ventilating apparatus, the gas necessary for the ventilation flows from the fresh gas metering unit of the ventilating apparatus into a breathing gas hose system which is connected to the patient via a Y-piece. The expiration branch of the hose system is connected to a controllable expiration valve.

The expiration valve is closed during the inspiratory phase so that the ventilating pressure during inhalation can build up in the hose system. However, in the expiratory phase, the expiration valve opens and the gas expired by the patient can flow out to the ambient. The control of the expiration valve is achieved with a bistable logic component which serves as a closure element, which, in rhythmic spacings, charges, during the inspiration phase, the control chamber of the expiration valve with a control pressure which closes the valve. For the expiration phase, a switchover to a second lower pressure level occurs by means of which a socalled PEEP-condition is generated in the hose system. PEEP is an acronym which stands for positive end expiratory pressure.

The two pressure levels are adjusted via two switchable branches generating a control pressure via the bistable logic component. Each branch includes a through-flow limiter and a flow throttle. The control gas flowing through the particular through-flow limiter flows off to the atmosphere through the outflow chamber of the closure element and the flow throttle with the developing backpressure functioning as a control pressure on the control chamber of the expiration valve. With the through-flow limiters, the inflowing control gas flow and thereby the control pressure can be varied. The control pressure for the inspiration phase and the ventilating phase can be adjusted separately with the through-flow limiters. The bistable logic component in the form of a closure element and the branches generating the control pressure conjointly define the control valve of the expiration valve.

The known control valve has the disadvantage that the least adjustable expiratory pressure is the atmospheric pressure since the control gas can only be released to the atmosphere. The control pressure adjustable at the control valve and thereby the reference pressure present in the control chamber of the breathing valve can be dropped only to the ambient atmosphere as a minimum. However, since the breathing gas encounters a dynamic resistance when flowing through the expiratory branch of the breathing gas line, there still always remains the dynamic flow resistance to be overcome in addition to the static reference pressure in the control chamber of the expiratory valve referred to the ambient atmosphere. Even for an adjusted desired value for the PEEP of atmospheric pressure, the actual pressure, which is to be overcome when exhaling, is the so-called dynamic PEEP. In this way, an additional dynamic PEEP pressure is present which has not been calibrated into the entire breathing system even in the presence of a pregiven adjustable PEEP pressure. The PEEP pressure can be different in accordance with the configuration of the ventilating apparatus. For this reason, uncontrollable discrepancies can occur between the adjusted PEEP pressure and the actual PEEP pressure.

SUMMARY OF THE INVENTION

It is an object of the invention to provide a expiration valve control arrangement which makes an expiration valve of the kind described above controllable so that the dynamic end expiratory overpressure for the adjustment of the PEEP is considered and compensated for.

According to a feature of the expiration valve control arrangement of the invention, the connection of the control valve extending from the inlet for the control gas includes a throttle for generating an underpressure. A pressure line extends from the throttle into the control chamber of the ventilating valve and the expiration chamber of the expiration valve is connected to a device for generating an underpressure. The throttle is advantageously configured so that it functions as a flow ejector and generates an underpressure in the pressure line with the underpressure being adjustable via the closure force of the closure element. If the full closure force operates on the closure element, an overpressure is generated in the pressure line which closes the expiration valve until the adjusted ventilating pressure during inhalation is reached. This occurs, for example, during the inspiratory phase.

The throttle of the control valve builds up a reference pressure in the control chamber of the expiration valve. The invention affords the advantage that this reference pressure can be reduced to the subatmospheric pressure present in the ventilating chamber as a minimum value. The subatmospheric pressure in the ventilating chamber is generated by the device for generating a subatmospheric pressure such as a suction pump. If the subatmospheric reference pressure and the subatmospheric pressure supplied by this device correspond to a previously determined dynamic flow resistance, then an end expiratory pressure can be obtained at the Y-piece of the hose system at atmospheric pressure during operation of the expiration valve even in the dynamic case. The unwanted dynamic end expiratory overpressure is thereby compensated. If the closure force applied to the closure element of the control valve is completely withdrawn (unthrottled control gas flow), the full subatmospheric reference pressure is transmitted into the control chamber of the expiration valve via the pressure line. With a subsequent adjustment of the closure force applied to the closure element of the control valve, this subatmospheric pressure is raised to such a level that it corresponds to the magnitude of the dynamic expiratory pressure and in this way compensates for the subsequent adjustment of the PEEP pressure. The full closure force acts on the closure element during inspiration. The reference pressure acting in the control chamber of the expiration valve closes the expiration valve until the previously adjusted ventilating pressure during inhalation is reached.

A suction pump is an advantageous device for generating the underpressure and can be either in the form of a volume-pumping pump or in the form of a flow ejector generating an underpressure.

According to another feature of the invention, the throttle is configured as a constriction changeable in its cross section. A different underpressure can be generated in the control chamber of the expiration valve in accordance with the adjustment of the cross section of the constriction. The change of the cross section can, for example, be achieved with different inserts or even with a slider element actuable from the outside which is introduced into the cross section of the throttle or by removing such a slider element. Even though every kind of constriction is suitable, it has been found however that a very good generation of an underpressure is achieved with the aid of a venturi nozzle.

The closure element of the control valve can include a plate membrane which partitions the outflow chamber from the pressure control chamber which likewise is provided with an outlet to the ambient.

It is advantageous to select a plunger coil arrangement which acts on the closure element with the aid of a rod. The plunger-coil arrangement applies a reliable closure force to the closure element of the control valve which is easily changed during the inhaling phase or during the exhaling phase.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
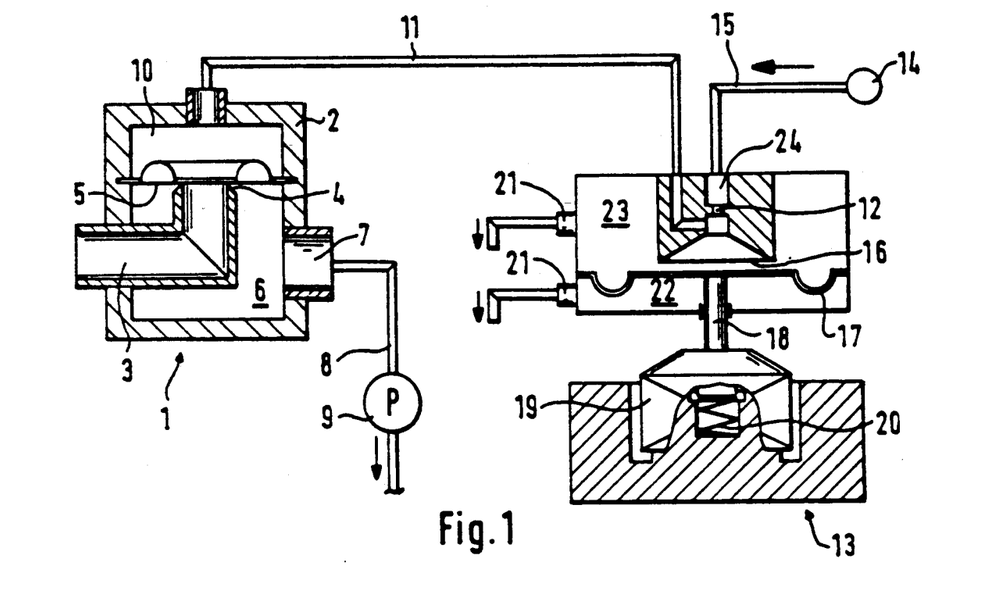
FIG. 1 is a schematic of the expiration valve control arrangement of the invention showing the interconnection between the expiration valve and the control valve equipped with a plunger-coil arrangement.

FIG. 1 discloses a expiration valve 1 having a valve housing 2 which includes an inlet 3 for the breathing gas from the expiratory branch of a breathing gas line (not shown). The inlet 3 opens into a crater valve seat 4 which is covered by a membrane 5. The valve chamber 6 of the expiration valve 1 has an outlet 7 which is connected via a suction line 8 with a device 9 for generating an underpressure. The device 9 can be a suction pump generating an underpressure and the outlet 7 is connected with the ambient through the suction line 8 and suction pump 9.

A pressure line 11 opens into the control chamber 10 of the expiration valve 1. The pressure line 11 has its starting point at throttle means 12 of the control valve 13. The throttle means 12 is supplied with a gas from a control gas source 14 and a control gas line 15 via an inlet 24. The opening of the throttle means 12 expands to define a crater seat 16 for accommodating a plate membrane 17 which is actuable by a plunger-coil arrangement 19 with the aid of a rod 18 applied to the plate membrane 17.

A closure force is applied to the plate membrane 17 by a pressure spring 20 via the rod 18. The closure force can be increased or partially reduced by means of the plunger-coil arrangement 19. When the control valve is opened, the control gas can flow off from the control gas source 14 and then out of the outflow chamber 23 of the control valve 13 via the outlet 21 to the ambient. The pressure control chamber 22 is also connected to the ambient via an outlet 21.

Figure 1A:
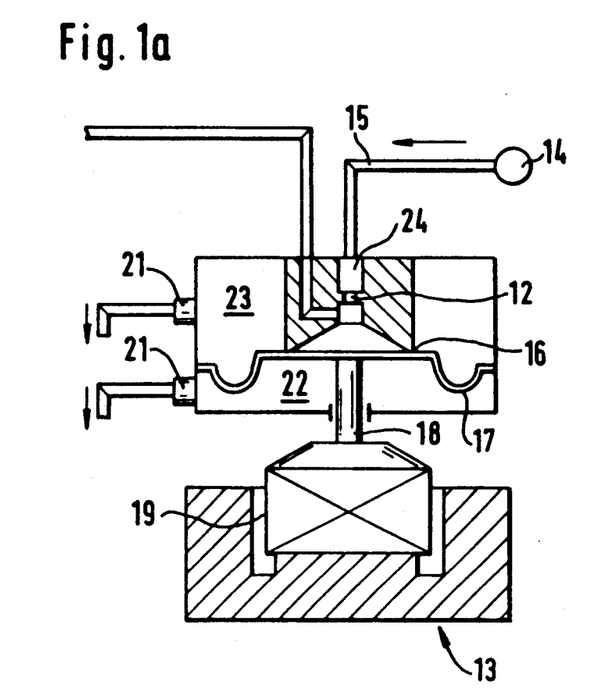
FIG. 1a is a view of the control valve of the expiration valve control arrangement of FIG. 1 showing the plate membrane of the control valve in its closed position.

During inspiration, the control valve 13 is closed as shown in FIG. 1a. The reference pressure acting in the control chamber 10 of the expiration valve 1 closes the expiration valve until the previously adjusted ventilating pressure during inhalation is reached.

Figure 2:
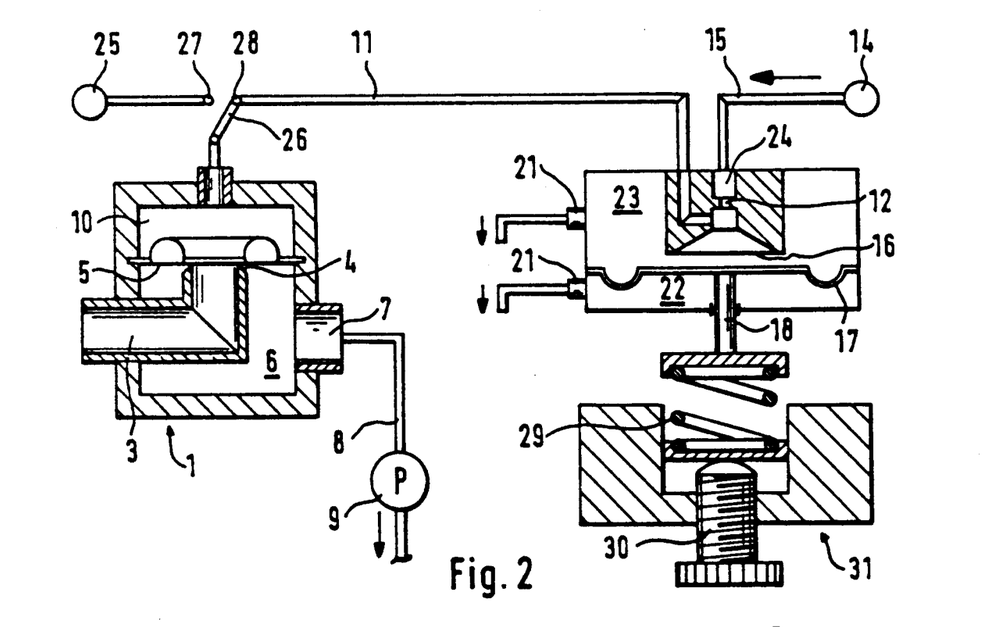
FIG. 2 is a schematic of another embodiment of the invention wherein the control valve includes a spring-biased control membrane.
Figure 2A:
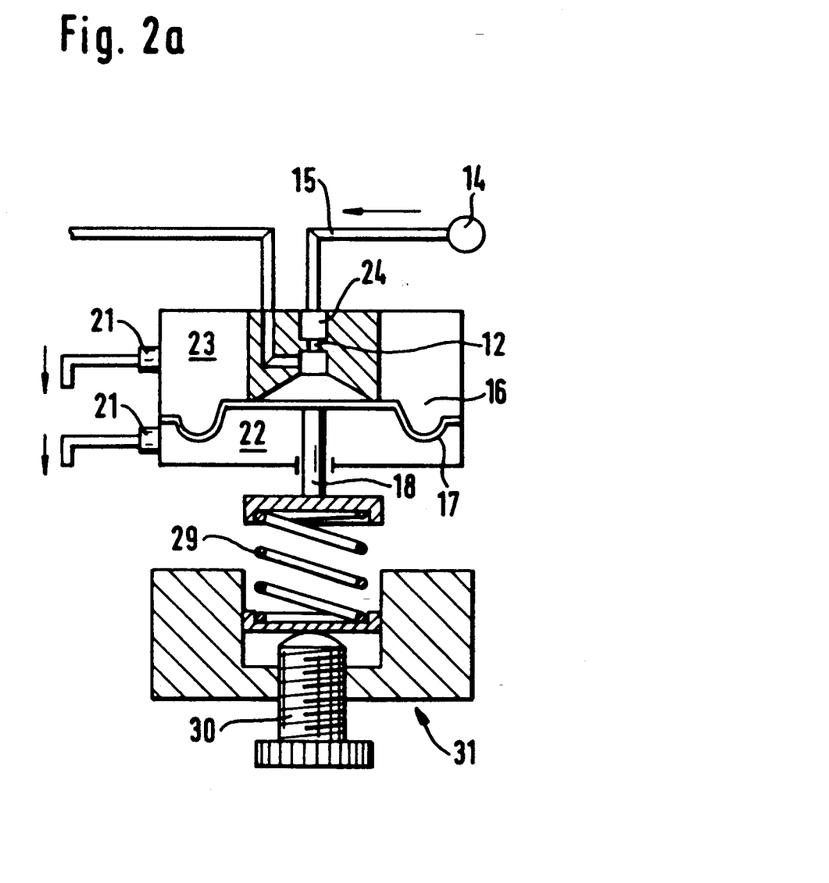
FIG. 2a is a view of the control valve of the expiration valve control arrangement of FIG. 2 showing the plate membrane of the control valve in its closed position; and, FIG. 2b shows the throwover switch of the expiration valve control arrangement of FIG. 2 shown connected to the first connecting port.

FIG. 2 shows an alternate embodiment having a spring-biased control valve 31. The reference numerals used in FIG. 2 are the same as those in FIG. 1 insofar as the same elements are utilized and the description for FIG. 1 applies analogously. In FIG. 2, the plate membrane 17 is shown in its open position; whereas in FIG. 2a, the plate membrane 17 is shown in its closed position.

Figure 2B:
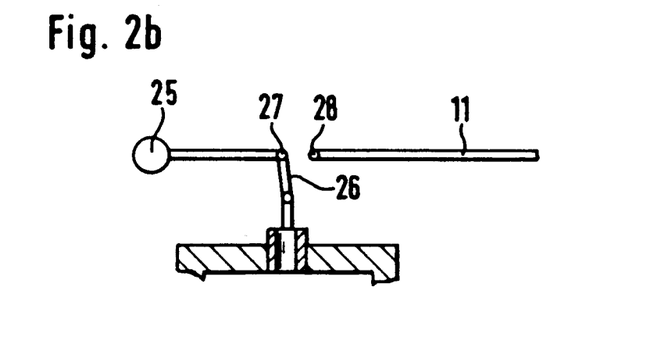

The plate membrane 17 is pretensioned by a spring 29 with the pretensioning being changeable with the knurled screw 30. Two control gas sources 25 and 14 are present. During inspiration, the throwover switch 26 is connected to the control gas source 25 via the first connecting port 27 as shown in FIG. 2b and the control chamber 10 is charged with the inspiration control pressure. The membrane 5 is in its closed position.

At the beginning of the expiratory phase, the control chamber 10 is connected to the pressure line 11 via the throwover switch 26 and the second connecting port 28. In the control chamber 10, the reference pressure produced by the closing force of the spring 29 is effective. The reference pressure and therefore the PEEP in the breathing gas hose system is adjustable by changing the pretensioning of spring 29 via the knurled screw 30.

It is understood that the foregoing description is that of the preferred embodiments of the invention and that various changes and modifications may be made thereto without departing from the spirit and scope of the invention as defined in the appended claims.

What is claimed is:

1. An expiration valve control arrangement for a ventilating apparatus having an expiration branch line, said expiration branch line producing dynamic flow resistance as the exhaled breathing gas flows therethrough, said dynamic flow resistance producing dynamic positive end expiratory pressure in the expiration branch line, the arrangement comprising:

an expiration valve having an expiration valve housing and membrane valve means for partitioning said housing into a control chamber and a valve chamber;

an inlet for admitting exhaled breathing gas into said valve chamber;

said membrane valve means being movable so as to close said inlet during inspiration and open said inlet during expiration so as to cause said inlet to communicate with said valve chamber;

means for compensating for said dynamic positive end expiratory pressure comprising;

control valve for generating a control pressure for maintaining a desired end expiratory pressure during expiration in said control chamber of said expiration valve, said control valve including a control valve housing and a plate membrane for partitioning said control valve housing into first and second chambers;

control gas supply means for supplying a control gas under pressure;

feed means for conducting said control gas into said control valve;

said control valve including valve seat means disposed in said first chamber and communicating with said feed means;

said plate membrane being mounted in said control valve housing for coacting with said valve seat means for opening and closing said valve seat means to said first chamber;

said feed means including throttle means disposed between said supply means and said valve seat means for throttling the flow of said control gas a conduit connecting said throttle means to said control chamber of said expiration valve for transmitting said control gas to said control chamber;

underpressure means for generating an underpressure in said valve chamber of said expiration valve corresponding to said dynamic positive end expiratory pressure; and, said control valve further including force applying means for applying a first force to said plate membrane during said inspiration for closing said valve seat means to said first chamber thereby causing the control gas flowing from said throttle means to produce an overpressure in said control chamber causing said membrane valve means of said expiration valve to close and for applying a second force to said control membrane during said expiration for opening said valve seat means to said first chamber, and said force applying means coating with said throttle means to adjust said desired end expiratory pressure in said control chamber causing said membrane valve means to open and permit exhalation, said second force being less than said first force and being adjustable to set said desired end expiratory pressure in said control chamber to compensate for said dynamic positive end expiratory pressure in the expiration branch line.

2. The expiration valve control arrangement of claim 1, said underpressure means comprising a suction pump connected to said first and second chambers and said valve chamber.

3. The expiration valve control arrangement of claim 1, said feed means defining a passage and said throttle means being a constriction formed in said passage.

4. The expiration valve control arrangement of claim 3, said passage having a first cross section and said constriction being formed by causing the cross section of said passage to be reduced to a preselected second cross section.

5. An expiration valve control arrangement for a ventilating apparatus, the arrangement comprising:

an expiration valve having an expiration valve housing and membrane valve means for partitioning said housing into a control chamber and a valve chamber;

said membrane valve means being movable so as to close during inspiration and open during expiration;

a control valve for generating a control pressure in said control chamber of said expiration valve, said control valve including a control valve housing and closure means for partitioning said control valve housing into first and second chambers;

control gas supply means for supplying a control gas under pressure;

feed means for conducting said control gas into said control valve;

said closure means including valve seat means disposed in said first chamber and communicating with said feed means; and, a closure member for coacting with said valve seat means for opening and closing said valve seat means to said first chamber;

said feed means including throttle means disposed between said supply means and said valve seat means for throttling the flow of said control gas;

a conduit for connecting said throttle means to said control chamber of said expiration valve;

underpressure means for generating an underpressure in said valve chamber of said expiration valve;

said closure means including force applying means for applying a first force to said closure member during said inspiration for closing said valve seat means to said first chamber thereby causing the control gas flowing from said throttle means to produce an overpressure in said control chamber causing said membrane valve means to close and for applying a second force to said closure member during said expiration for opening said valve seat means to said first chamber and to coact with said throttle means to produce an underpressure in said control chamber causing said membrane valve means to open, said second force being less than said first force and being adjustable to set said underpressure to a predetermined value;

said closure member being a plate membrane partitioning said first chamber from said second chamber;

said force applying means being an actuator for actuating said plate membrane; and, said first chamber being an outflow chamber having an outlet communicating with the ambient and said second chamber being a control chamber likewise having an outlet communicating with the ambient.

6. The expiration valve control arrangement of claim 5, said actuator comprising a plunger-coil arrangement having a movable push rod connected to said plate membrane; and, resilient biasing means for biasing said plate membrane against said valve seat means.

7. The expiration valve control arrangement of claim 6, said resilient biasing means being a pressure spring interposed between said push rod and said control valve housing.

8. An expiration valve control arrangement for a ventilating apparatus, the arrangement comprising:

an expiration valve having an expiration valve housing and membrane valve means for partitioning said housing into a control chamber and a valve chamber;

said membrane valve means being movable so as to close during inspiration and open during expiration;

a control valve for generating a control pressure in said control chamber of said expiration valve, said control valve including a control valve housing and closure means for partitioning said control valve housing into first and second chambers;

first control gas supply means for supplying a first control gas at a first control pressure;

second control gas supply means for supplying a second control gas at a second control pressure;

feed means for conducting said second control gas into said control valve;

said closure means including valve seat means disposed in said first chamber and communicating with said feed means; and, a closure member for coacting with said valve seat means for opening and closing said valve seat means to said first chamber;

said feed means including throttle means disposed between said supply means and said valve seat means for throttling the flow of said second control gas;

a conduit for conducting said second control gas away from said throttle means;

switchover means movable into a first switching position for connecting said first control gas supply means to said control chamber of said expiration valve means and then movable out of said first switching position and into a second switching position for connecting said conduit to said control chamber of said expiration valve during expiration;

underpressure means for generating an underpressure in said valve chamber of said expiration valve;

said closure means including force applying means for applying a force to said closure member acting in the closure direction during said expiration for coacting with said throttle means to produce an underpressure in said control chamber causing said membrane valve means to open; and, means for adjusting said force to set said underpressure to a predetermined value.

9. An expiration valve control arrangement for a ventilating apparatus, the arrangement comprising:

an expiration valve having an expiration valve housing and membrane valve means for partitioning said housing into a control chamber and a valve chamber;

an inlet for admitting breathing gas into said valve chamber;

said membrane valve means being movable so as to close said inlet during inspiration and open said inlet during expiration so as to cause said inlet to communicate with said valve chamber;

a control valve for generating a control pressure for maintaining a desired end expiratory pressure during expiration in said control chamber of said expiration valve, said control valve including a control valve housing and closure means for partitioning said control valve housing into first and second chambers;

control gas supply means for supplying a control gas under pressure;

feed means for conducting said control gas into said control valve;

said closure means including valve seat means disposed in said first chamber and communicating with said feed means; and, a closure member for coacting with said valve seat means for opening and closing said valve seat means to said first chamber;

said feed means including throttle means disposed between said supply means and said valve seat means for throttling the flow of said control gas;

a conduit for connecting said throttle means to said control chamber of said expiration valve;

underpressure means for generating an underpressure in said valve chamber of said expiration valve;

said closure means including force applying means for applying a first force to said closure member during said inspiration for closing said valve seat means to said first chamber thereby causing the control gas flowing from said throttle means to produce an overpressure in said control chamber causing said membrane valve means to close and for applying a second force to said closure member during said expiration for opening said valve seat means to said first chamber and to coact with said throttle means to produce an underpressure in said control chamber causing said membrane valve means to open, said second force being less than said first force and being adjustable to set said underpressure to a predetermined value; and, said first chamber being an outflow chamber having an outlet communicating with the ambient and said second chamber being a control chamber likewise having an outlet communicating with the ambient.

10. An expiration valve control arrangement for a ventilating apparatus, the arrangement comprising:

an expiration valve having an expiration valve housing and membrane valve means for partitioning said housing into a control chamber and a valve chamber;

said membrane valve means being movable so as to close during inspiration and open during expiration;

a control valve for generating a control pressure in said control chamber of said expiration valve, said control valve including a control valve housing and closure means for partitioning said control valve housing into first and second chambers;

control gas supply means for supplying a control gas under pressure;

feed means for conducting said control gas into said control valve;

said closure means including valve seat means disposed in said first chamber and communicating with said feed means; and, a closure member separate from said throttle means for coacting with said valve seat means for opening and closing said valve seat means to said first chamber;

said feed means including throttle means disposed between said supply means and said valve seat means for throttling he flow of said control gas;

a conduit for connecting said throttle means to said control chamber of said expiration valve;

underpressure means for generating an underpressure in said valve chamber of said expiration valve;

said closure means including force applying means for applying a first force to said closure member during said inspiration for closing said valve seat means to said first chamber thereby causing the control gas flowing from said throttle means to produce an overpressure in said control chamber causing said membrane valve means to close and for applying a second force to said closure member during said expiration for opening said valve seat means to said first chamber and to coact with said throttle means to produce an underpressure in said control chamber causing said membrane valve means to open, said second force being less than said first force and being adjustable to set said underpressure to a predetermined value;

said closure member being a plate membrane partitioning said first chamber from said second chamber; and, said force applying means being an actuator for actuating said plate membrane.

11. The expiration valve control arrangement of claim 10, said first chamber being an outflow chamber having an outlet communicating with the ambient and said second chamber being a control chamber likewise having an outlet communicating with the ambient.

* * * * *

UNITED STATES PATENT AND TRADEMARK OFFICE
CERTIFICATE OF CORRECTION

PATENT NO. : 5,065,746

DATED : November 19, 1991

INVENTOR(S) : Hans-Wilhelm Steen

It is certified that error appears in the above-identified patent and that said Letters Patent is hereby corrected as shown below:

In the title page, under Assignee: after "Drägerwerk" insert -- Aktiengesellschaft --.

In column 1, line 53: delete "ventilating" and substitute -- expiration -- therefor.

In column 2, line 28: delete "ventilating" and substitute -- expiration -- therefor.

In column 2, line 28: delete "expiration" and substitute -- ventilating -- therefor.

In column 2, line 52: between "at" and "atmospheric", insert -- the --.

In column 5, line 2: delete ";" and substitute -- : -- therefor.

In column 5, line 3: before "control valve" insert -- a --.

In column 5, line 23: after "gas" insert -- ; --.

In column 5, line 42: delete "and".

In column 5, line 42: delete "coating" and substitute -- coacting -- therefor.

UNITED STATES PATENT AND TRADEMARK OFFICE
CERTIFICATE OF CORRECTION

PATENT NO. : 5,065,746

DATED : November 19, 1991

INVENTOR(S) : Hans-Wilhelm Steen

It is certified that error appears in the above-identified patent and that said Letters Patent is hereby corrected as shown below:

In column 7, line 27: between "valve" and "means" insert -- during inspiration to close said membrane valve --.

In column 8, line 55: delete "he" and substitute -- the -- therefor.

Signed and Sealed this

Twenty-seventh Day of April, 1993

Attest:

MICHAEL K. KIRK

Attesting Officer

Acting Commissioner of Patents and Trademarks